United States Patent [19]

Weigel et al.

[11] Patent Number: 4,831,145

[45] Date of Patent: May 16, 1989

[54] 7-PHENYLSULFONYLOXYMETHYLENE-6-OXO-PERHYDROQUINOLINES

[75] Inventors: Leland O. Weigel, Indianapolis; Gilbert S. Staten, Camby, both of Ind.

[73] Assignee: Eli Lilly and Company, Indianapolis, Ind.

[21] Appl. No.: 197,712

[22] Filed: May 23, 1988

Related U.S. Application Data

[62] Division of Ser. No. 845,916, Mar. 31, 1986, Pat. No. 4,764,609.

[51] Int. Cl.$^4$ .......................................... C07D 215/20
[52] U.S. Cl. ................................................... 546/164
[58] Field of Search ........................................ 546/164

[56] References Cited

U.S. PATENT DOCUMENTS

| 4,367,231 | 1/1983 | Kornfeld et al. | 546/164 |
| 4,501,890 | 2/1986 | Nichols et al. | 514/267 |

FOREIGN PATENT DOCUMENTS 0241186 10/1987 European Pat. Off. ............ 546/164

OTHER PUBLICATIONS

Corey et al., "Total Synthesis . . . Hybridalactone", *J. Am. Chem. Soc.*, 106, 2735–2736 (1984).

*Primary Examiner*—David B. Springer
*Attorney, Agent, or Firm*—Robert A. Conrad; Leroy Whitaker

[57] ABSTRACT

This invention provides a process for preparing trans 2-aminopyrimido[4,5-g]quinolines employing novel intermediates.

6 Claims, No Drawings

7-PHENYLSULFONYLOXYMETHYLENE-6-OXO-PERHYDROQUINOLINES

This application is a division of application Ser. No. 845,916, filed 3-31-86, now U.S. Pat. No. 4,764,609.

SUMMARY OF THE INVENTION

The present invention provides a convenient method for converting cycloalkanones to 2-aminopyrimidines. More specifically, the present invention provides a process for preparing the trans-($\pm$)-racemate of a compound of the formula

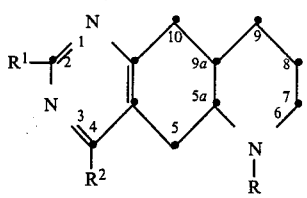

I wherein R is hydrogen, cyano, $C_1$-$C_3$ alkyl or allyl; $R^1$ is amino, —$NHR^3$ or —$NR^4R^5$; $R^2$ is hydrogen or methyl; $R^3$ is methyl, ethyl, n-propyl, $C_1$-$C_3$ alkyl-CO, phenyl-CO or substituted phenyl-CO, wherein said substituents are 1 or 2 members selected from the group consisting of chloro, fluoro, bromo, methyl, ethyl, methoxy, ethoxy and trifluoromethyl; and $R^4$ and $R^5$ are individually methyl, ethyl or n-propyl, which comprises reacting the trans-($\pm$)-racemate of a compound of the formula

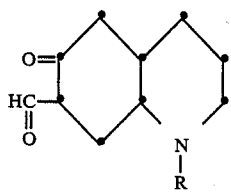

with a sulfonate derivative of the formula

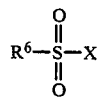

wherein $R^6$ is $C_1$-$C_3$ alkyl, phenyl, 4-chlorophenyl, 4-bromophenyl, or 4-methylphenyl and X is halogen, in a suitable polar, aprotic solvent to provide a compound of the formula

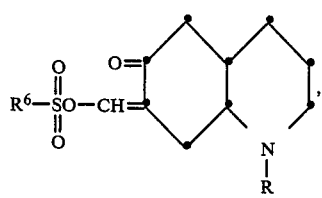

which is reacted with guanidine carbonate.

Another embodiment of the present invention are intermediates employed in the present process. More specifically, the present invention provides the trans-($\pm$)-racemate of a compound of the formula

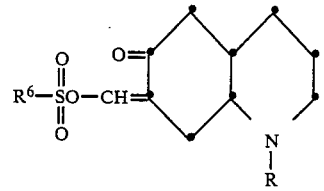

wherein:
R is hydrogen, cyano, $C_1$-$C_3$ alkyl or allyl; and
$R^6$ is $C_1$-$C_3$ alkyl, phenyl, 4-chlorophenyl, 4-bromophenyl or 4-methylphenyl.

The present invention also provides a process for preparing a trans-(—)-isomer of the formula

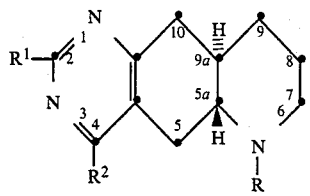

II wherein R is hydrogen, cyano, $C_1$-$C_3$ alkyl or allyl; $R^1$ is amino, —$NHR^3$ or —$NR^4R^5$; $R^2$ is hydrogen or methyl; $R^3$ is methyl, ethyl, n-propyl, $C_1$-$C_3$ alkyl-CO, phenyl-CO or substituted phenyl-CO, wherein said substituents are 1 or 2 members selected from the group consisting of chloro, fluoro, bromo, methyl, ethyl, methoxy, ethoxy and trifluoromethyl; and $R^4$ and $R^5$ are individually methyl, ethyl or n-propyl, which comprises reacting a compound of the formula

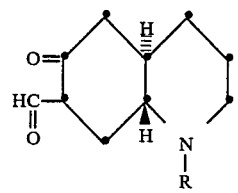

with a sulfonate derivative of the formula

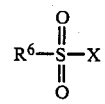

wherein $R^6$ is $C_1$-$C_3$ alkyl, phenyl, 4-chlorophenyl, 4-bromophenyl, or 4-methylphenyl and X is halogen, in a suitable polar, aprotic solvent to provide a compound of the formula

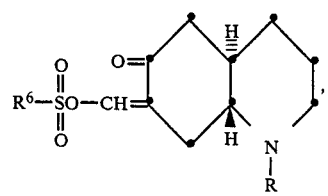

which is reacted with guanidine carbonate.

The present invention also provides a trans-(—)-isomer of the formula

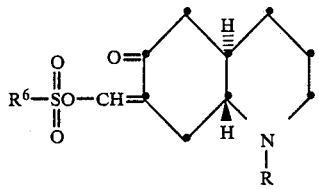

wherein:
R is hydrogen, cyano, $C_1$-$C_3$ alkyl or allyl; and
$R^6$ is $C_1$-$C_3$ alkyl, phenyl, 4-chlorophenyl, 4-bromophenyl or 4-methylphenyl.

DETAILED DESCRIPTION OF THE INVENTION

The term $C_1$-$C_3$ alkyl, as used herein, represents a straight or branched alkyl chain bearing from one to three carbon atoms. $C_1$-$C_3$ Alkyl groups are methyl, ethyl, n-propyl and isopropyl.

Halogen represents fluoro, chloro, bromo and iodo.

The compounds of formula I have two asymmetric centers, one at position 5a and another at position 9a. The compounds may exist as 4-stereoisomers occurring as two diastereoisomeric pairs or racemates. One diastereoisomeric pair is the cis racemate, wherein both of the hydrogen atoms at the 5a and 9a positions are on the same side of the plane created by the perhydroquinoline ring. The other diastereoisomeric pair is the trans racemate, wherein the hydrogen atoms at the 5a and 9a positions are on opposite sides in relation to the plane of the perhydroquinoline ring. This invention provides a process for preparing the trans racemate trans-($\pm$)-2-amino-6-substituted-5,5a,6,7,8,9,9a,10-octahydropyrimido[4,5-g]quinoline of formula I.

The trans-($\pm$)-racemate is composed of the trans-($-$)-stereoisomer represented by formula II and the trans-($+$)-stereoisomer represented by formula IIa. These individual stereoisomers are reproduced below:

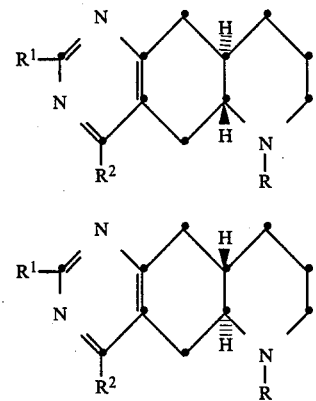

It is known that most, if not all, of the dopaminergic activity of the trans-($\pm$)-racemate exists in the trans-($-$)-enantiomer. Therefore, the present process may also be used to synthesize trans-($-$)-2-amino-6-substituted-5,5a,6,7,8,9,9a,10-octahydropyrimido[4,5-g]qui represented by Formula II.

Further, the intermediates employed in the two above described processes are provided as yet another embodiment of the present invention. The novel intermediates employed to synthesize the trans-($\pm$)-racemates of compounds of formula I are the trans-($\pm$)-racemates of compounds of the formula

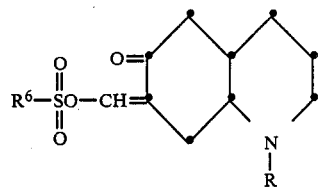

wherein R and $R^6$ are as defined above. The novel intermediates used in the process for preparing the trans-($-$)-isomers of formula II are the trans-($-$)-isomers of the formula

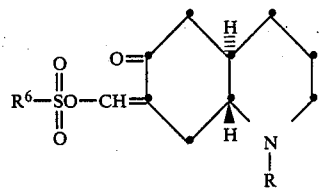

wherein R and $R^6$ are as defined above.

While the entire scope of variables taught herein are believed operable, the present invention does have preferred aspects. In the above formulae, R is preferably $C_1$-$C_3$ alkyl, and especially n-propyl. Further, $R^2$ is preferably hydrogen, $R^1$ is preferably amino and $R^6$ is preferably 4-methylphenyl. Other preferred process conditions will be noted hereinafter.

In the first step of the process of the present invention the 6-oxo-7-formyldecahydroquinoline starting materials defined above is reacted with a sulfonate derivative in a suitable polar, aprotic solvent to provide a novel intermediate of the invention.

The sulfonate derivative employed in the present process and as defined above is present at a concentration in the range of about 1.0 to about 2.0 molar equivalents for each molar equivalent of the 6-oxo-7-formyldecahydroquinoline starting material employed. More preferably, merely a slight excess of sulfonate is used, that is from about 1.1 molar equivalents to about 1.5 molar equivalents for each molar equivalent of 6-oxo-7-formyldecahydroquinoline starting material.

The process of the invention is conducted in a suitable polar, aprotic solvent. Typical polar, aprotic solvents suitable for use herein include tetrahydrofuran, N,N-dimethylformamide, dimethylsulfoxide, acetonitrile and the like. The amount of solvent employed in the process is not critical, but no more than necessary to solubilize the starting materials need be used, or a slight excess.

The first step of the process of the invention is substantially complete after about 10 minutes to about 2 hours when conducted at a temperature in the range of about $-80°$ C. to about $20°$ C., more specifically after about one hour when conducted at a temperature in the range of about $-40°$ C. to about $0°$ C.

The intermediates of the invention are preferably not isolated, but rather used directly in the second step of the present process.

In the second step of the process of the invention the novel intermediate of the invention, prepared in the first step of the invention as described above, is reacted with guanidine carbonate to afford a 2-aminopyrimido[4,5-g]quinoline. It has been determined that the present novel intermediate should be added to the guanidine carbonate mixture so as to maximize the yield of the octahydroquinoline derivative. While an equimolar amount of guanidine carbonate may be used in the process, an excess of guanidine carbonate is preferably employed.

The process of the invention is substantially complete after about 1 hour to about 24 hours when conducted at a temperature in the range of about 0° C. to about 100° C., more preferably after about 4 to 16 hours when conducted at a temperature between about 15° C. and about 40° C.

The product of the present process may be isolated by standard procedures following substantial completion of the reaction. Preferably, the volatile constituents are evaporated, typically under vacuum, and the residue is slurried in water and combined with a suitable acid such as hydrochloric acid. The aqueous phase is washed with a water immiscible organic solvent and the solution is made basic with a suitable base. The aqueous phase is extracted with a water immiscible organic solvent, and the organic extracts are combined and concentrated under vacuum. The residue may be further purified, if desired, by standard techniques, for example purification over solid supports such as silica gel or alumina, or crystallization from common solvents such as methanol or ethyl acetate.

The compounds prepared by the process of the present invention wherein R is $C_1-C_3$ alkyl or allyl, and their pharmaceutically acceptable acid addition salts, are dopamine (D-2) agonists substantially devoid of other agonist or antagonist activities. As such, the compounds are useful in the treatment of hypertention, depression, anxiety, Parkinson's disease and disease states characterized by an excess of prolactin secretion such as galactorrhea and inappropriate lactation. These uses are discussed in detail in U.S. Pat. No. 4,501,890.

In addition to the biological activities described above, the compounds are also useful in the treatment of sexual dysfunction in mammals, and such use is taught in U.S. Pat. No. 4,521,421.

The compounds prepared by the present process wherein R is H or CN are useful as intermediates to the compounds described above wherein R is $C_1-C_3$ alkyl or allyl. Compounds wherein R is CN can be hydrolyzed in acetic acid and zinc dust to provide compounds wherein R is hydrogen. Compounds wherein R is hydrogen may then be conveniently alkylated with a lower alkyl halide, or allylated with an allyl halide, according to standard procedures to provide compounds having the biological activities described above.

The trans 6-oxo-7-formyldecahydroquinoline compounds employed as starting materials in the present process are known in the art and readily prepared by prior art processes. These compounds are preferably prepared by reacting either the trans-(±)-racemate or trans-(−)-stereoisomer of 6-oxodecahydroquinoline with an alkyl formate in the presence of a base and a mutual solvent. The general process conditions are described for these reactions in U.S. Pat. No. 4,567,266, herein incorporated by reference. The synthesis of the trans-(±)-racemate of 6-oxodecahydroquinoline is taught and claimed in U.S. Pat. No. 4,540,787 starting with a 6-alkoxyquinoline. Resolution of the trans-(±)-racemate to the corresponding trans-(−)-stereoisomer of 6-oxodecahydroquinoline is taught and claimed in U.S. Pat. No. 4,471,121 employing optically active di-p-toluoyltartaric acid.

The following Examples further illustrate the process of the present invention. The Examples are not intended to be limiting to the scope of the invention in any respect and should not be so construed.

EXAMPLE 1

Synthesis of trans-(−)-5,5a,6,7,8,9,9a,10-octahydro-6-(n-propyl)pyrimido[4,5-g]quinoline-2-amine A. trans-(−)Octahydro-7-[[[(4-methylphenyl)-sulfonyl]oxy]methylene]-1-(n-propyl)-6(2H)-quinolin A 1 l. 3-neck round bottom flask was purged with nitrogen and charged with 35.0 g (0.312 mol) of potassium t-butoxide. Next, 348 ml of dry tetrahydrofuran was added to the flask and the resulting mixture was cooled to about −15° C. with stirring. To this mixture was added a solution of 30.3 g (0.155 mol) of (8aR-trans)-(−)-octahydro-1-(n-propyl)-6(2H)-quinolinone in 30 ml of tetrahydrofuran over a period of about 9 minutes while maintaining the temperature of the reaction mixture between about −15° C. and about −17° C. The stirred reaction mixture was allowed to warm to room temperature and the mixture was stirred for 1 hour. The reaction mixture was cooled to about −25° C. and a solution of 23.1 g (25.2 ml, 0.31 mol) of ethyl formate in 45 ml of tetrahydrofuran was added dropwise to the reaction mixture over a period of about 21 minutes. The resulting mixture was stirred for about 30 minutes at about −25° C. and was allowed to warm to about 5° C. The mixture was cooled to about −15° C. and held at that temperature for about 60 hours. The mixture was warmed to about 0° C. and charged with 8.9 ml of glacial acetic acid dropwise. The stirred reaction mixture was cooled to about −37° C. To the mixture was added a solution of 32.6 g (0.171 mol) of p-toluenesulfonyl chloride dissolved in 45 ml of tetrahydrofuran over a period of about 5 minutes. The reaction mixture was warmed to about 0° C. over a period of about 65 minutes and the mixture was held at this temperature for 17.5 hours. The title compound thus prepared was held in situ for further processing.

B. A 2 l. 3-neck round bottom flask which had been purged with nitrogen was charged with 69.7 g (0.387 mol) of guanidine carbonate and 440 ml of dry N,N-dimethylformamide. The resulting mixture was heated to approximately 55° C. with stirring and the solution containing trans-(−)-octahydro-7-[[[(4-methylphenyl)-sulfonyl]oxy]methylene)-1-(n-propyl)-6(2H)-quin prepared above was added dropwise over a period of about 52 minutes. The reaction mixture was cooled to room temperature and allowed to stir at this temperature for approximately 16 hours. The reaction mixture was concentrated under vacuum, and the resulting residue was cooled to room temperature and charged with 400 ml of water and 35 ml of methanol. The mixture was cooled to about 5° C. To the mixture was added 6N hydrochloric acid dropwise and, when the mixture became unstirrable, 100 ml of methanol was added. The addition of the hydrochloric acid was continued until a total of 200 ml had been added. The resulting mixture was warmed to about 25° C. and the methanol was removed under vacuum. The mixture was washed four times with 90 ml portions of chloroform. The aqueous layer was combined with 390 ml of chloroform and 38 ml of 50% sodium hydroxide was added to provide a pH of 12.6. The organic phase was separated and the aqueous phase was extracted with 195 ml of chloroform. The organic layers were combined and dried over 15 g of anhydrous sodium sulfate. The solution was concentrated under vacuum and the residue was transferred to a 500 ml round bottom flask fitted with a mechanical stirrer. The residue was combined with 100 ml of methanol and the resulting mixture was refluxed for approximately 1 hour. The mixture was cooled to approximately 5° C. for 30 minutes and filtered under vacuum. The collected solid was washed with cold methanol and vacuum dried under nitrogen overnight to provide 27.8 g of trans-(−)-5,5,6a,7,8,9,9a,10-octahydro-6-(n-propyl)-pyrimido[4,5-g]quinoline-2Yield 72.9%. An optical rotation was recorded for this compound employing methanol as the solvent, and the following results were obtained:

589 nm = −150°
365 nm = −407.6°

EXAMPLE 2

Synthesis of trans-(−)-5,5a,6,7,8,9,9a,10-octahydro-6-(n-propyl)pyrimido[4,5-g]quinoline-2-amine A. trans-(−)-Octahydro-7-[[[(4-methylphenyl)-sulfonyl]oxy]methylene]-1-(n-propyl)-6(2H)-quinoli A 22 l. round bottom bottom flask was charged with 568.9 g (5.07 mol) of potassium t-butoxide under a nitrogen atmosphere. To the flask was added 4.1 l of dry tetrahydrofuran and the resulting slurry was cooled to approximately −25° C. To the slurry was added 500.0 g (2.56 mol) of (8aR-trans)-(−)-octahydro-1-(n-propyl)-6(2H)-quinolinone over a period of 15 minutes. The addition funnel was rinsed twice with 30 ml portions of dry tetrahydrofuran and the mixture was allowed to warm to about 12° C. over a period of about 90 minutes. The mixture was warmed to about 25° C. and held at that temperature for about one hour. The mixture was cooled to about −26° C. and 386.8 g (422 ml, 5.22 mol) of ethyl formate was added to the mixture dropwise over a period of about 30 minutes. The mixture was held at about 0° C. overnight, cooled to about −8° C. and 150.0 g of glacial acetic acid was added to the stirred mixture. The pH of the mixture was about 11 following addition of the acid. The mixture was cooled to about −40° C. and a solution of 534.3 g (2.8 mol) of p-toluenesulfonyl chloride in 1610 ml of dry tetrahydrofuran was added rapidly while maintaining the temperature below about −35° C. The mixture was warmed to about 0° C. and held at this temperature for about one hour. The tetrahydrofuran was evaporated from the mixture under vacuum and 2.46 l. of dry DMF was added. The resulting solution containing trans-(−)-octahydro-7-[[[(4-methylphenyl)sulfonyl]oxy]methylene]-1-(n-propyl)-6(2H)-quinolinone was held for further processing.

B. To a second 22 l. round bottom flask containing 7.77 l. of DMF at about 55° C. was added 1.147 kg (6.37 mol) of guanidine carbonate under nitrogen. The reaction mixture from the first flask containing trans-(−)-octahydro-7-[[[(4-methylphenyl)sulfonyl]oxy]methylene] was added to the contents of the second flask over about 65 minutes at a temperature of about 55° C. The mixture was allowed to cool to room temperature and was stirred at room temperature overnight. The reaction mixture was concentrated under vacuum and the residue was transferred to a 22 l. round bottom flask and combined with 6.6 l. of water. To the resulting slurry was added 3.1 l. of 6N hydrochloric acid to provide a final pH of about 1.5. The aqueous solution was washed 4 times with 1.5 l. portions of chloroform. Next, 6 l. of chloroform was added to the mixture and the pH was adjusted to about 12.6 with 680 ml of 50% sodium hydroxide (w:w). The organic phase was separated and the aqueous phase was extracted twice with 4 l. portions of warm chloroform. The organic phases were combined and dried over anhydrous sodium sulfate. The volatile constituents were evaporated under vacuum and the residue was refluxed in 1.65 l. of methanol. The mixture was cooled in an ice bath for about 1 hour and the precipitated solid was collected by vacuum filtration. The solid was washed twice with 200 ml portions of cold methanol and vacuum dried overnight to provide 417.9 g of the title compound. The compound was further purified to provide 413.7 g of a total yield of 65.0%. The identity of the product was verified by thin layer chromatography employing a solvent system consisting of chloroform:methanol:sodium hydroxide (84:15:1, v:v:v) as compared to an authentic reference standard.

We claim:

1. A trans-(±)-racemate of a compound of the formula

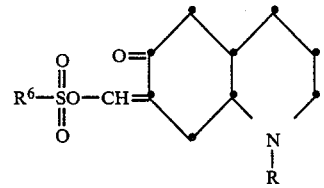

wherein:
R is hydrogen, cyano, $C_1$-$C_3$ alkyl or allyl; and
$R^6$ is $C_1$-$C_3$ alkyl, phenyl, 4-chlorophenyl, 4-bromophenyl or 4-methylphenyl.

2. A compound of claim 1 wherein R is n-propyl.

3. A compound of claim 2 wherein $R^6$ is 4-methylphenyl.

4. A trans-(−)-isomer of the formula

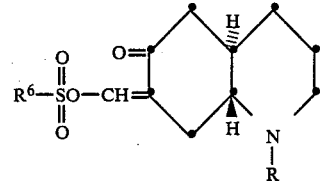

wherein:
R is hydrogen, cyano, $C_1$-$C_3$ alkyl or allyl; and
$R^6$ is $C_1$-$C_3$ alkyl, phenyl, 4-chlorophenyl, 4-bromophenyl or 4-methylphenyl.

5. A compound of claim 4 wherein R is n-propyl.

6. A compound of claim 5 where $R^6$ is 4-methylphenyl.

* * * * *